United States Patent [19]

Shawkat

[11] Patent Number: 5,648,089

[45] Date of Patent: Jul. 15, 1997

[54] EXTRACT SOLUTION AND HERBAL MIXTURE FOR TREATMENT OF HEPATITIS

[76] Inventor: Tarek Shawkat, 4018 Leah La., Mays Landing, N.J. 08330

[21] Appl. No.: 498,699

[22] Filed: Jul. 3, 1995

[51] Int. Cl.$^6$ .................... A61K 9/14; A61K 9/08
[52] U.S. Cl. ............ 424/434; 424/195.1; 424/489; 514/894
[58] Field of Search .................... 424/434, 464, 424/489, 195.1

[56] References Cited

U.S. PATENT DOCUMENTS 4,673,575  6/1987  Venkateswaran et al. ......... 424/195.1

*Primary Examiner*—Thurman K. Page
*Assistant Examiner*—James M. Spear
*Attorney, Agent, or Firm*—Panitch Schwarze Jacobs & Nadel, P.C.

[57] ABSTRACT

A newly formulated herbal mixture and herbal nasal drops are provided for ethical use and treatment of vital hepatitis diseases. The herbal formulation is in two parts, which may be used separately or together, including (1) an oral herbal formulation including coarse granules of 9 herbs, ground and added together in specific ratios; and (2) nasal drops prepared from the extract of a single herb, namely Ecballium Elaterium A. Rich.

3 Claims, No Drawings

EXTRACT SOLUTION AND HERBAL MIXTURE FOR TREATMENT OF HEPATITIS

BACKGROUND OF THE INVENTION

The following is a combination of herbs which has never been used as a group for treatment of Hepatitis-B and Hepatitis-C liver disease.

This Group of herbs have been a part of folk medicine and traditional medicine used for other ailments individually but never with the following arrangement and combination for a treatment of Hepatitis-C and Hepatitis-B disease. They also are used in combination with the liquid extract of one more herb in a special fashion, (regimen).

This group of herbs has been tried with success in clearing the viral D.N.A. from patients with Hepatitis-B and Hepatitis-C as used as a whole group.

SUMMARY OF THE INVENTION

In October 1993, I developed that herbal combination, that's to follow, together with the invention of nasal drops of a separate herb that was used with the other combination for treating patients diagnosed with active Hepatitis-B and patients diagnosed with active Hepatitis-C, with good results.

The herbal combination includes the following:
a) Phyllanthus Embilca L.
b) Terminalia Chebiola RETZ
c) Cichorium Intyus L.
d) Carthanus Tincorius L.
e) Solenostemma Argel Hayne
f) Nigella Sativa L.
g) Erythraea Centaurium Pers
h) Cynara Cardunculus Var. Scoly
i) Rheuon of officinale Baill The above combination of herbs (a) through (i) are used orally i.e. per mouth.

j) Ecballium Elaterium A. Rich

The herb (j) is used in a nasal form.

DETAILED DESCRIPTION OF PREFERRED EMBODIMENTS

Manufacturing

The oral herbal combination, herbs (a) through (i) are formed from the following ratio of dried plants by weight.

a) Forty percent of weight of the above said mixture is from the dried fruit of Phyllanthus Embilca L.
b) Ten percent of weight of the above said mixture is from the dried fruit of Terminalia Chebiola RETZ.
c) Seven percent of weight of the above said mixture comes from the plant Cichorium Intyus L., excluding the roots.
d) Ten percent of weight of the above said mixture comes from the flower of the plant Carthamus Tincorius L.
e) Three percent of weight of the above said mixture comes from the plant Solenostemma Argel Hayne, excluding the roots.
f) Ten percent of the above said mixture comes from the seeds of Nigella Saliva L.
g) Five percent of weight of the above said mixture comes from the plant Erythraea Centaurium Pers, excluding the roots.
h) Ten percent of weight of the above said mixture comes from the stem and leaves of the plant Cynara Cardunculus Var. Scoly.
i) Five percent of weight of the above said mixture comes from (Rhisome) i.e. (the stem) of Rheuon officinale Baill.

The mixture of the above herbs is put together in the above mentioned ratio by weight and ground to coarse mixture and used orally.

The nasal drops are manufactured by adding one liter of distilled water to every one kg. of the fruit of the plant Ecballium Elaterium A. Rich. The mixture is squeezed and the extract is sterilized by filtration using Zedtis filter or sterilized by adding Thiomersal in the ratio of 0.05 grams for every liter of the above mentioned solution.

Dosage (how to use it)

1. Herbs (a) through (i) are taken by mouth three times a day, each dose is five grams.
2. The nasal drops (Solution from herb (j) are used one drop in each nostril twice a day.
3. Both the mixture of herbs (a) through (i) and the nasal drops are used concomitantly for a period of two months and can be repeated according to the patient's response to the treatment.
4. They also can be used as two separate drugs i.e. (the mixture without the nasal drops) according to the response of the patient.

Effects

The effects are:
1. The mixture of the oral herbs results in stimulation of liver cells to regenerate.
2. Blood cholesterol reducing effect.
3. Increasing Bilirubin secretion and excretion.
4. Stimulation of lymphocytic system of the body and increasing immune response which results in clearance of vital D.N.A. In patients who suffer from active viral Hepatitis-B and Hepatitis-C. This has been noted by testing patient's sera for viral D.N.A by P.C.R. technique, before and miter using the herbal combination as mentioned above.

Side Effects

The side effects are:
1. As mentioned before these herbs have been a part of folk medicine and have been used for different human ailments and no toxicity has been associated with any of them that is reportable.

However, as the group of herbs added together the only noted side effects included:
a) Bad taste
b) Mild flatulence For the nasal drops:
a) Throat congestion and pain if swallowed.
b) Sneezing
c) Flu-like symptoms
d) Mild fever
e) Mild diarrhea, (if swallowed)

How Supplied

1. The oral herbs (a) through (i) are supplied as the purified forms of the herbs in granular shape in sealed packages of 250 grams or 500 grams. The mixture is kept in a cool dry storage away from the sunlight.
2. The nasal drops are supplied in plastic nasal droppers of 30 and 60 ml. and refrigerated at all times at four degrees centigrade.

I claim:

1. An herbal combination for the treatment of viral hepatitis diseases, comprising a mixture for oral administration of the following dried plants in the following ratio, all percentages being percent by weight of the mixture:

(a) 40 percent from the dried fruit of Phyllanthus Embilca L.;

(b) 10 percent from the dried fruit of Terminalia Chebiola RETZ;

(c) 7 percent from the plant Cichorium Intyus L., excluding the roots;

(d) 10 percent from the flower of the plant Carthamus Tincorius L.

(e) 3 percent from the plant Solenostemma Argel Hayne, excluding the roots;

(f) 10 percent from the seeds of Nigella Sativa L.;

(g) 5 percent from the plant Erythraea Centaurium Pers, excluding the roots;

(h) 10 percent from the stem and leaves of the plant Cynara Cardunculus Var. Scoly; and (i) 5 percent from the rhisome (stems) of Rheuon officinale Baill.

2. The herbal combination of claim 1, further comprising nasal drops for administration together with the oral mixture, the nasal drops comprising an extract of the fruit of the plant Ecballium Elaterium A. Rich.

3. A composition for treatment of viral hepatitis diseases comprising an aqueous solution for nasal administration, said solution comprising an extract of the fruit of the plant Ecballium Elaterium A. Rich.

* * * * *